(12) United States Patent
Lee et al.

(10) Patent No.: US 8,078,248 B2
(45) Date of Patent: Dec. 13, 2011

(54) DIGITAL LOGIC MODULE OF OXIMETER SENSOR PROBE

(75) Inventors: Chao-Fa Lee, Taipei (TW); Shih-Jung Chang, Taipei (TW); Cheng-Hsing Kuo, Taipei (TW)

(73) Assignee: Tatung Company, Taipei (TW)

( * ) Notice: Subject to any disclaimer, the term of this patent is extended or adjusted under 35 U.S.C. 154(b) by 1204 days.

(21) Appl. No.: 11/819,186

(22) Filed: Jun. 26, 2007

(65) Prior Publication Data

US 2008/0161663 A1 Jul. 3, 2008

(30) Foreign Application Priority Data

Dec. 29, 2006 (TW) .............................. 95149949 A

(51) Int. Cl.
*A61B 5/1455* (2006.01)

(52) U.S. Cl. ....................................... 600/323; 600/322
(58) Field of Classification Search ........... 600/309–344
See application file for complete search history.

(56) References Cited

U.S. PATENT DOCUMENTS 4,819,752 A * 4/1989 Zelin ............................. 600/322
5,246,002 A * 9/1993 Prosser .......................... 600/336

* cited by examiner

*Primary Examiner* — Eric Winakur
*Assistant Examiner* — Marjan Fardanesh
(74) *Attorney, Agent, or Firm* — Bacon & Thomas, PLLC

(57) ABSTRACT

A digital logic module of oximeter sensor probe includes a detection probe, an operation circuit, and an integrated circuit. This digital logic module of oximeter sensor probe is provided with the light source driving function and the light source capturing function for reducing loading of the microprocessor, so that a cheaper microprocessor can be used in the oximeter sensor for reducing the development cost of the oximeter.

10 Claims, 3 Drawing Sheets

DIGITAL LOGIC MODULE OF OXIMETER SENSOR PROBE

BACKGROUND OF THE INVENTION

1. Field of the Invention

This invention relates to a probe module and, more particularly, to a digital logic module of oximeter sensor probe.

2. Description of Related Art

Generally, the conventional oximeter takes an external blood oxygenation signal to measure blood oxygenation level, by using a photodiode to detect an infrared and a red light transilluminated through the human body. Further, the oximeter will separate the infrared and the red light to perform amplifying for converting the analog signal to digital signal so as to perform operation to obtain the blood oxygenation level of a human body.

FIG. 1 illustrates a block diagram showing the conventional oximeter 10. The microprocessor 100 connects to the light emitting control circuit 110, the magnification amplifying control circuit 130, and the operation circuit 140, wherein the light emitting control circuit 110 connects to the light emitting unit 122 of the probe 120. The light emitting unit 122 comprises a red light source RED and an infrared light source IR, and the operation circuit 140 connects to the light sensitive element 121 of the probe 120. The light source driving program of the microprocessor 100 can generate a light source driving signal a1 to the light emitting control circuit 110 for controlling the red light source RED and the infrared light source IR of the light emitting unit 122. The microprocessor 100 can generate a light source pulse width modulation signal pwm to adjust brightness of the red light source RED and the infrared light source IR. The light source signal capturing program of the microprocessor 100 can generate a light source capturing signal a2 to the operation circuit 140. The operation circuit 140 controls the capturing cycle of the light source signal c1 of the light sensitive element 121 in the probe 120 based on the light source capturing signal a2. After emitting the red light source RED and the infrared light source IR to a finger of tester, the light source signal c1 is provided with blood oxygenation level. Further, the microprocessor 100 can control the magnification amplifying control circuit 130 to amplify the light source signal c1 of the operation circuit 140, and the operation circuit 140 can demodulate the light source signal c1 for being converted to a digital signal d1 through the A/D conversion. Finally, the microprocessor 100 will receive the digital signal d1 to perform operation for obtaining the value of the blood oxygenation level.

Although the implementation of such oximeters has been achieved, the light source driving program and the light source capturing program of the microprocessor 100 will occupy too much resource, resulting in causing inconvenience to the user and also increasing resource consumption during the operation period.

SUMMARY OF THE INVENTION

The object of the invention is to provide the light source driving function and the light source capturing function to the digital logic module of oximeter sensor probe for reducing resource consumption.

To achieve the object, the present invention provides a digital logic module of oximeter sensor probe connected to an external microprocessor for receiving a control signal, a first light source pulse width modulation signal, a second light source pulse width modulation signal, and a timing output signal from the microprocessor for analysis to obtain a value of blood oxygenation level. The digital logic module of oximeter sensor includes: a detection probe including a light emitting unit and a light sensitive element, the light emitting unit having a first wavelength light source and a second wavelength light source, the light sensitive element capturing lights generated by the first wavelength light source and the second wavelength light source for being transformed into a first electrical signal and a second electrical signal respectively; an operation circuit electrically connected to the light sensitive element of the detection probe for receiving the first electrical signal and the second electrical signal to perform amplifying, demodulating, filtering, and analog-to-digital converting so as to generate a first digital signal and a second digital signal for being transmitted to the microprocessor; and an integrated circuit including a light source driving unit and a light source capturing unit, the light source driving unit electrically connecting to the microprocessor and the first wavelength light source and the second wavelength light source of the light emitting unit, respectively, the light source capturing unit electrically connecting to the microprocessor and the operation circuit, respectively.

The microprocessor outputs the control signal, the first light source pulse width modulation signal, the second light source pulse width modulation signal, and the timing output signal for driving the light source driving unit and the light source capturing unit to output a data signal to the microprocessor, or to output a first light source driving signal and a second light source driving signal to the first wavelength light source and the second wavelength light source respectively for controlling light emitting cycle, and a first light source capturing signal and a second light source capturing signal to the operation circuit for periodically capturing the first electrical signal and the second electrical signal.

DETAILED DESCRIPTION OF THE PREFERRED EMBODIMENT

Figure 1:
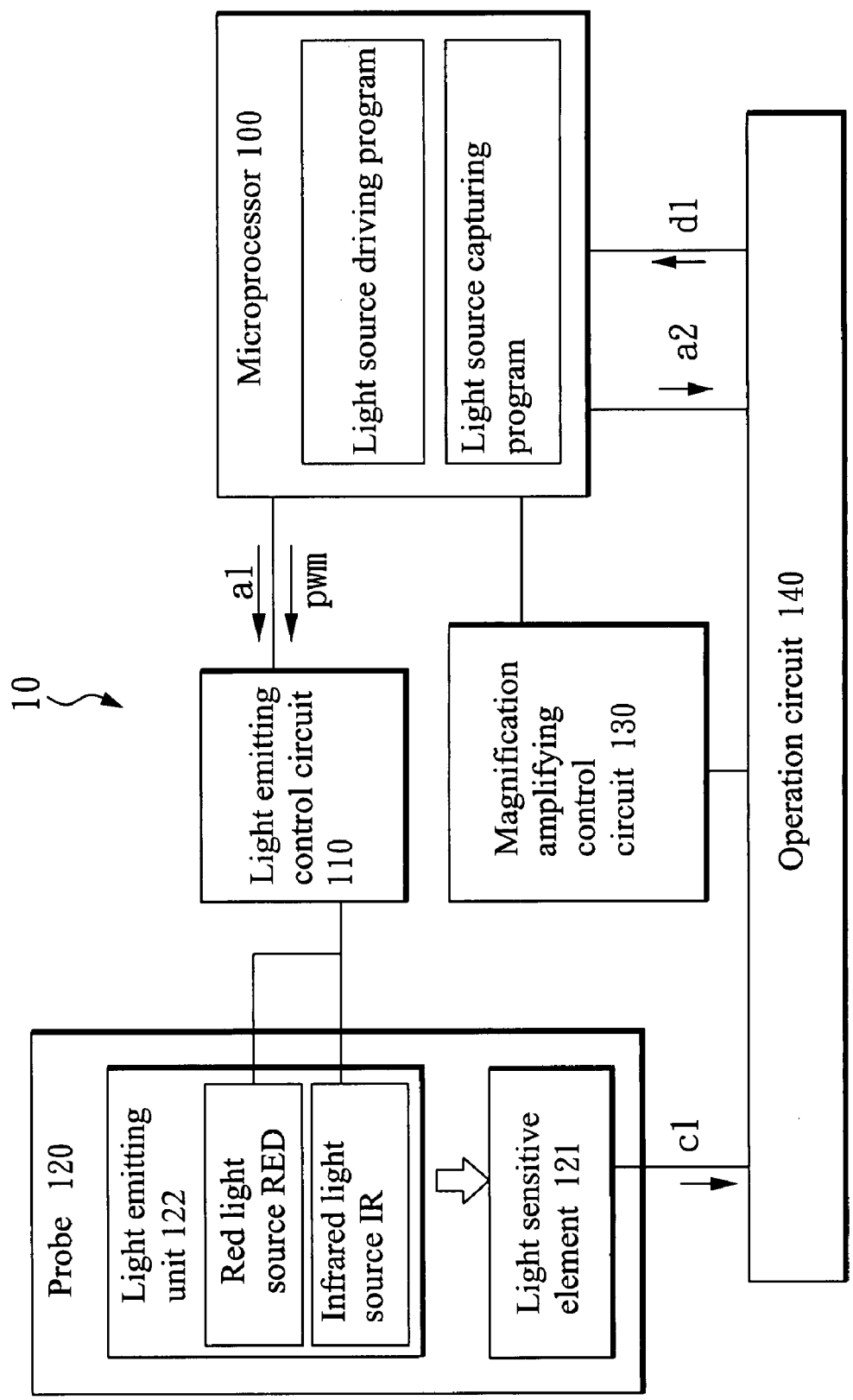
FIG. 1 illustrates a block diagram showing the conventional oximeter.
Figure 2:
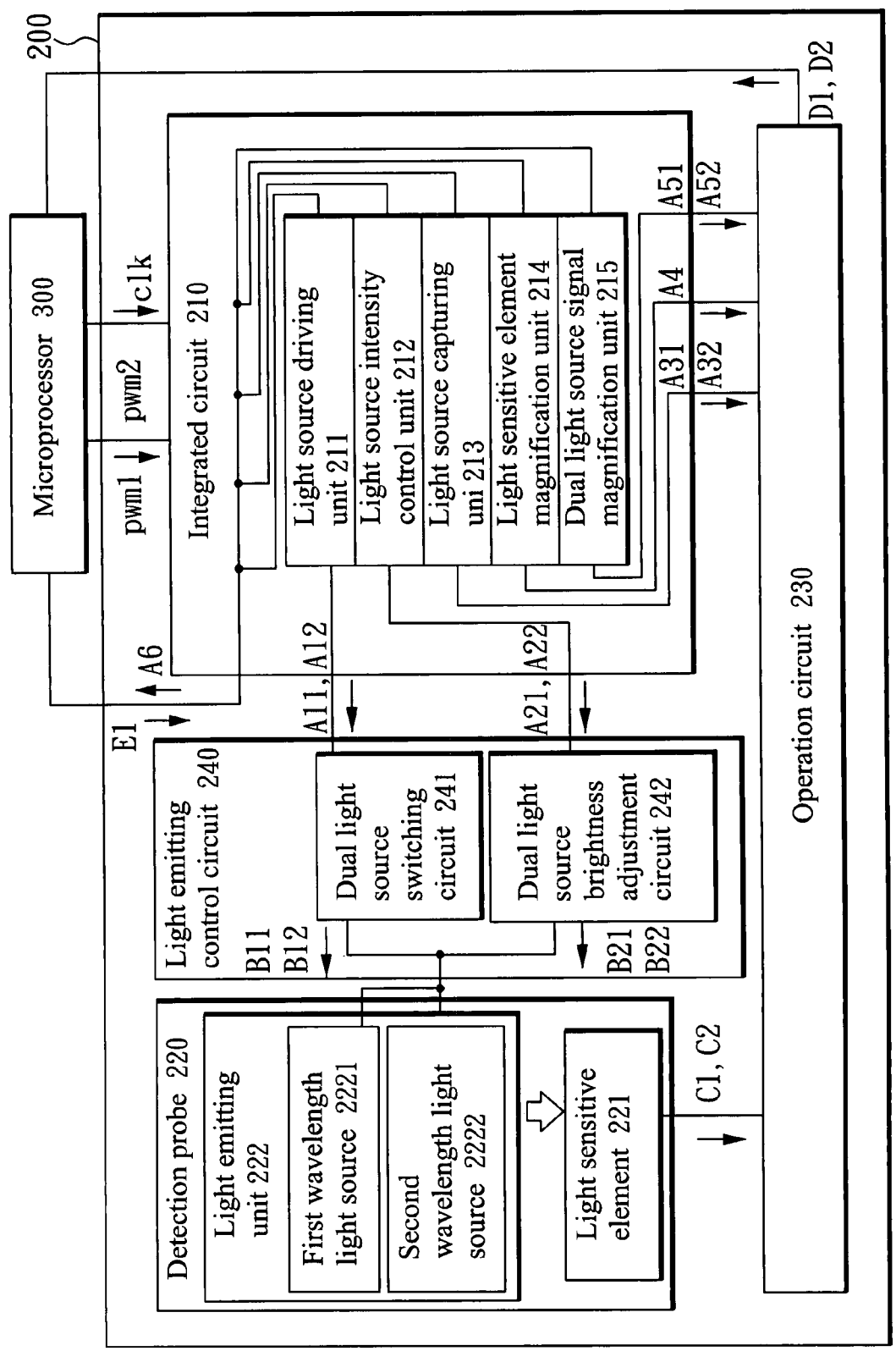
FIG. 2 is a block diagram of a digital logic module of oxygen saturation probe according to the preferred embodiment of the present invention.

FIG. 2 is a block diagram of a digital logic module of oximeter sensor probe according to the preferred embodiment of the present invention.

Referring to FIG. 2, the digital logic module of oximeter sensor probe 200 connects to an external microprocessor 300 for receiving the control signal E1, the first light source pulse width modulation signal pwm1, the second light source pulse width modulation signal pwm2, and the timing output signal clk from the microprocessor 300. The microprocessor 300 receives a frequency generated by an external oscillator (not shown in figure) to generate the timing output signal clk. The microprocessor 300 receives a signal outputted by the digital logic module of oximeter sensor probe 200 to perform operation for obtaining a value of blood oxygenation level. Furthermore, the digital logic module of oximeter sensor probe 200 includes a detection probe 220, an operation circuit 230, an integrated circuit 210, and a light emitting control circuit 240. The timing output signal clk can produce a four phase controlled sequence to control a red light emitting and captured, and an infrared light emitting and captured.

The detection probe 220 includes a light emitting unit 222, and a light sensitive element 221. The light emitting unit 222 includes a first wavelength light source 2221, and a second wavelength light source 2222. The light sensitive element 221 captures lights of the first wavelength light source 2221 and the second wavelength light source 2222 for transforming the same into a first electrical signal C1 and a second electrical signal C2 respectively. In this embodiment, the detection probe 220 is an oximeter sensor; the first wavelength light source 2221 generates a red light; the second wavelength light source 2222 generates an infrared.

The operation circuit 230 electrically connects to the light sensitive element 221 of the detection probe 220 for receiving the first electrical signal C1 and the second electrical signal C2 to perform amplifying, demodulating, filtering, and analog-to-digital converting so as to generate a first digital signal D1 and a second digital signal D2 corresponding thereto for being transmitted to the microprocessor 300 for analysis.

The integrated circuit 210 includes a light source driving unit 211, a light source capturing unit 213, a light source intensity control unit 212, a light sensitive element magnification unit 214, and a dual light source signal magnification unit 215. The light source driving unit 211 electrically connects to the microprocessor 300 and the first wavelength light source 2221 and the second wavelength light source 2222 of the light emitting unit 222, respectively. The light source capturing unit 213 electrically connects to the microprocessor 300 and the operation circuit 230, respectively. In addition, the light source intensity control unit 212 connects to the microprocessor 300 and the probe 220, respectively, for receiving the first light source pulse width modulation signal pwm1 and the second light source pulse width modulation signal pwm2 for generating a first light source intensity signal A21 and a second light source intensity signal A22, so as to adjust intensities of the first wavelength light source 2221 and the second wavelength light source 2222. Further, the light sensitive element magnification unit 214 electrically connects to the microprocessor 300 and the operation circuit 230, respectively, for generating a light sensitive element magnification signal A4 to the operation circuit 230. The dual light source signal magnification unit 215 electrically connects to the microprocessor 300 and the operation circuit 230, respectively, for generating a first light source magnification signal A51 and a second light source magnification signal A52 to the operation circuit 230. The timing output signal clk is the reference signal of the first light source driving signal A11, the second light source driving signal A12, the first light source capturing signal A31 and the second light source capturing signal A32.

The light emitting control circuit 240 includes a dual light source switching circuit 241 and a dual light source brightness adjustment circuit 242. The dual light source switching circuit 241 electrically connects to the light source driving unit 211 of the integrated circuit 210 and the first wavelength light source 2221 and the second wavelength light source 2222 of the probe 220, respectively, for receiving the first light source driving signal A11 and the second light source driving signal A12 to generate a first light source switching signal B11 and a second light source switching signal B12 for being transmitted to the first wavelength light source 2221 and the second wavelength light source 2222 of the probe 220 for controlling the light emitting cycle. The first wavelength light source 2221 and the second wavelength light source 2222 emit light at different time based on respective light emitting cycle. In addition, the dual light source brightness adjustment circuit 242 connects to the light source intensity control unit 212 of the integrated circuit 210 and the first wavelength light source 2221 and the second wavelength light source 2222 of the light emitting unit 222, respectively. The dual light source brightness adjustment circuit 242 receives the first light source intensity signal A21 and the second light source intensity signal A22 for generating a first light source adjustment signal B21 and a second light source adjustment signal B22 to the first wavelength light source 2221 and the second wavelength light source 2222 of the light emitting unit 222 respectively for adjusting intensity of the light source.

In this embodiment, the microprocessor 300 outputs a control signal E1 to the integrated circuit 210 for setting the dual light source driving cycle, the dual light source capturing cycle, a light sensitive element magnification, and a dual light source signal magnification. After setting the abovementioned values, the integrated circuit 210 will generate a data signal A6 including a light source driving cycle value of the light source driving unit 211, a light source capturing cycle value of the light source capturing unit 213, a light sensitive element magnification value of the light sensitive element magnification unit 214, a light source signal magnification value of the dual light source signal magnification unit 215, and a light source brightness value of the light source intensity control unit 212 to the microprocessor 300.

Figure 3:
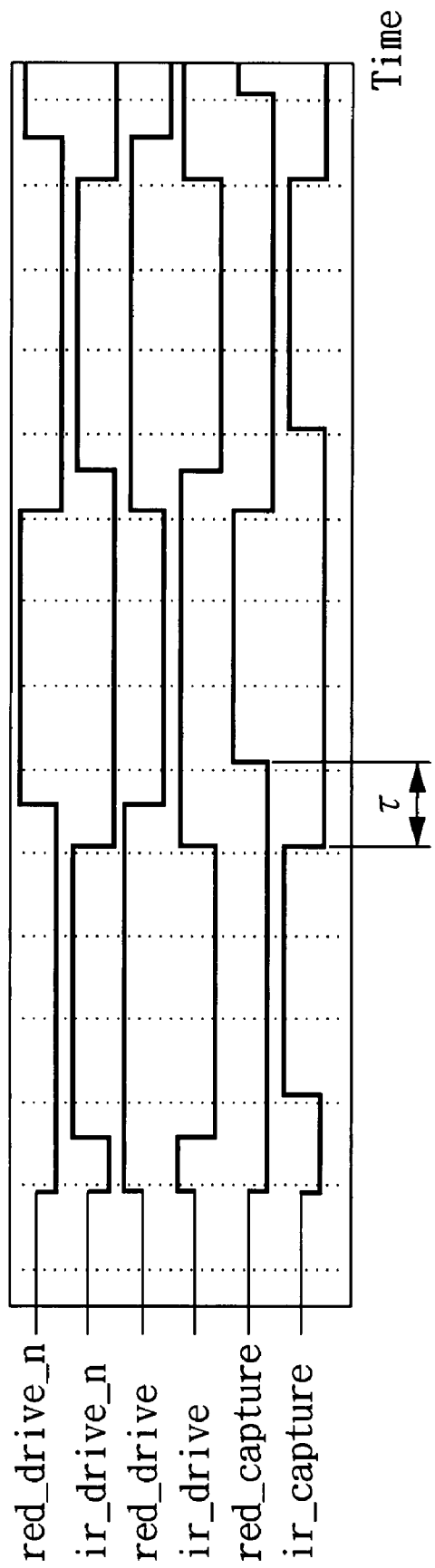
FIG. 3 shows a schematic diagram of light source driving cycle and the light source capturing cycle of the present invention.

FIG. 3 shows a schematic diagram of light source driving cycle and the light source capturing cycle of the present invention. Referring to FIG. 3, the red-drive and the red-drive-n represent the driving cycles at two ends of the red light source, respectively, and the waveforms thereof are opposite and symmetrical to each other based on the first light source driving signal A11. The ir-drive and the ir-drive-n represent the driving cycles at two ends of the infrared light source, respectively, and the waveforms thereof are opposite and symmetrical to each other based on the second light source driving signal A12. Compared the red-drive-n with the ir-drive-n, while the light source maintains in the active status, the red-drive-n or the ir-drive-n will keep in high level status. Therefore, while the red light source maintains in active status, the infrared light source keeps in inactive status, and vice versa. Please refer to FIG. 3, the red-capture represents a red light capturing cycle based on the first light source capturing signal A31, and the ir-capture represents the infrared capturing cycle based on the second light source capturing signal A32. As shown in FIG. 3, a time difference τ between the red light capturing cycle and the infrared capturing cycle can avoid receiving other signals, surges, or noises so as to increase the accuracy of blood oxygenation level.

In this embodiment, the microprocessor 300 outputs the control signal E1, the first light source pulse width modulation signal pwm1, the second light source pulse width modulation signal pwm2, and the timing output signal clk for driving the light source driving unit 211 and the light source capturing unit 213 to respectively output a data signal A6 to the microprocessor 300, or to respectively output a first light source driving signal A11 and a second light source driving signal A12 to the first wavelength light source and the second wavelength light source of the light emitting unit 222 of the detection probe 220, and a first light source capturing signal A31 and a second light source capturing signal A32 to the operation circuit 230 to perform periodical light emitting and capturing for capturing the first electrical signal C1 and the second electrical signal C2 so as to correspondingly generate a first digital signal D1 and a second digital signal D2 for being transmitted to the microprocessor 300 for analysis. The operation of the digital logic module of oximeter sensor probe 200 will be described thereinafter.

For measuring blood oxygenation level, the tester should put his/her finger to the detection probe 220. The light source intensity control unit 212 of the integrated circuit 210 can receive the first light source pulse width modulation signal pwm1 and the second light source pulse width modulation signal pwm2 outputted by the microprocessor 300 for setting the first light source intensity signal A21 and the second light source intensity signal A22 to the dual light source brightness adjustment circuit 242 of the light emitting control circuit 240 for generating the first light source adjustment signal B21 and the second light source adjustment signal B22. In addition, the first light source adjustment signal B21 and the second light source adjustment signal B22 will be transmitted to the red light source and the infrared light source of the detection probe 220 for adjusting light source intensity. After emitting the red light or the infrared to the finger, the light sensitive element 221 will receive a first electrical signal C1 corresponding to the red light and a second electrical signal C2 corresponding to the infrared for being transmitted to the operation circuit 230. The light sensitive element magnification unit 214 of the integrated circuit 210 can receive the control signal E1 outputted by the microprocessor 300 for setting the light sensitive element magnification value of the data signal A6 so as to generate a light sensitive element magnification signal A4 to the operation circuit 230 for amplifying the first electrical signal C1 and the second electrical signal C2 to reach a workable level. Finally, the dual light source magnification unit 215 of the integrated circuit 210 can receive the control signal E1 for setting the dual light signal magnification value of the data signal A6 so as to adjust the levels of the two electrical signals. After adjusting signal level, the first electrical signal C1 and the second electrical signal C2 will be respectively converted into a first digital signal D1 and a second digital signal D2 through the A/D conversion. The microprocessor 300 will receive the first digital signal D1 and the second digital signal D2 to analyze for obtaining a blood oxygenation level.

In view of the foregoing, it is known that the present invention can provide the light source driving function and the light source capturing function to the digital logic module of oximeter sensor probe for reducing loading of the microprocessor. Therefore, a cheaper microprocessor can be used in the oximeter sensor for reducing the development cost of the oximeter sensor. Further, a time difference τ between the red light capturing cycle and the infrared capturing cycle can avoid receiving other signals, surges, or noises so as to increase the accuracy of the blood oxygenation level.

Although the present invention has been explained in relation to its preferred embodiment, it is to be understood that many other possible modifications and variations can be made without departing from the spirit and scope of the invention as hereinafter claimed.

What is claimed is:

1. A digital logic module of oximeter sensor probe connected to an external microprocessor for receiving a control signal, a first light source pulse width modulation signal, a second light source pulse width modulation signal, and a timing output signal from the microprocessor for analysis to obtain a value of blood oxygenation level, the digital logic module of oximeter sensor probe comprising:

a detection probe including a light emitting unit and a light sensitive element, the light emitting unit having a first wavelength light source and a second wavelength light source, the light sensitive element capturing lights generated by the first wavelength light source and the second wavelength light source for being transformed into a first electrical signal and a second electrical signal respectively;

an operation circuit electrically connected to the light sensitive element of the detection probe for receiving the first electrical signal and the second electrical signal to perform amplifying, demodulating, filtering, and analog-to-digital converting so as to generate a first digital signal and a second digital signal for being transmitted to the microprocessor; and an integrated circuit including a light source driving unit and a light source capturing unit, the light source driving unit electrically connecting to the microprocessor and the first wavelength light source and the second wavelength light source of the light emitting unit, respectively, the light source capturing unit electrically connecting to the microprocessor and the operation circuit, respectively;

wherein the microprocessor is configured to output the control signal, the first light source pulse width modulation signal, the second light source pulse width modulation signal, and the timing output signal for driving the light source driving unit and the light source capturing unit to output a data signal to the microprocessor in a first mode, and, to output a first light source driving signal and a second light source driving signal to the first wavelength light source and the second wavelength light source respectively for controlling light emitting cycle, and a first light source capturing signal and a second light source capturing signal to the operation circuit for periodically capturing the first electrical signal and the second electrical signal in a second mode.

2. The digital logic module of oximeter sensor probe as claimed in claim 1, wherein the timing output signal is a reference signal for the first light source driving signal, the second light source driving signal, the first light source capturing signal and the second light source capturing signal.

3. The digital logic module of oximeter sensor probe as claimed in claim 1, further comprising a light emitting control circuit having a dual light source switching circuit, wherein the dual light source switching circuit electrically connects to the integrated circuit, and the first wavelength light source and the second wavelength light source of the light emitting unit of the detection probe, respectively, for receiving the first light source driving signal and the second light source driving signal to correspondingly generate a first light source switching signal and a second light source switching signal for being transmitted to the first wavelength light source and the second wavelength light source of the detection probe, respectively, for controlling light emitting cycle.

4. The digital logic module of oximeter sensor probe as claimed in claim 3, wherein the integrated circuit further comprises a light source intensity control unit, and the light emitting control circuit further comprises a dual light source brightness adjustment circuit, the light source intensity control unit receiving the first light source pulse width modulation signal and the second light source pulse width modulation signal for setting the first light source intensity signal and the second light source intensity signal for being transmitted to the dual light source brightness adjustment circuit of the light emitting control circuit, the dual light source brightness control unit generating a first light source adjustment signal and a second light source adjustment signal for being transmitted to the first wavelength light source and the second wavelength light source of the detection probe for adjusting light source intensity.

5. The digital logic module of oximeter sensor probe as claimed in claim 1, wherein the integrated circuit further comprises a light sensitive element magnification unit electrically connected to the microprocessor and the operation circuit for generating a light sensitive element magnification signal to the operation circuit.

6. The digital logic module of oximeter sensor probe as claimed in claim 5, wherein the integrated circuit further comprises a dual light source signal magnification unit electrically connected to the microprocessor and the operation circuit for generating a first light source magnification signal and a second light source magnification signal to the operation circuit.

7. The digital logic module of oximeter sensor probe as claimed in claim 6, wherein the data signal includes a light source driving cycle value of the light source driving unit, a light source capturing cycle value of the light source capturing unit, a light sensitive element magnification value of the light sensitive element magnification unit, a light source signal magnification value of the dual light source signal magnification unit, and a light source intensity value of the light source intensity control unit.

8. The digital logic module of oximeter sensor probe as claimed in claim 7, wherein the control signal sets the dual light source driving cycle value, the dual light source capturing cycle value, a light sensitive element magnification value, and the dual light source signal magnification value.

9. The digital logic module of oximeter sensor probe as claimed in claim 1, wherein the detection probe is an oximeter sensor.

10. The digital logic module of oximeter sensor probe as claimed in claim 1, wherein the first wavelength light source and the second wavelength light source emit light at different time based on respective light emitting cycle.

* * * * *